(12) United States Patent
Basheer et al.

(10) Patent No.: US 10,499,123 B2
(45) Date of Patent: Dec. 3, 2019

(54) SENSOR BUS ARCHITECTURE FOR MODULAR SENSOR SYSTEMS

(71) Applicant: urban-gro, Inc., Lafayette, CO (US)

(72) Inventors: Mohammed Rana Basheer, Costa Mesa, CA (US); Atul A. Patel, Irvine, CA (US)

(73) Assignee: urban-gro, Inc., Lafayette, CO (US)

( * ) Notice: Subject to any disclaimer, the term of this patent is extended or adjusted under 35 U.S.C. 154(b) by 143 days.

(21) Appl. No.: 15/626,085

(22) Filed: Jun. 17, 2017

(65) Prior Publication Data

US 2017/0363451 A1    Dec. 21, 2017

Related U.S. Application Data

(60) Provisional application No. 62/351,989, filed on Jun. 19, 2016.

(51) Int. Cl.
*H04Q 9/00*     (2006.01)
*G01N 33/24*    (2006.01)
(Continued)

(52) U.S. Cl.
CPC .............. *H04Q 9/00* (2013.01); *G01D 18/00* (2013.01); *G01D 21/00* (2013.01); *G01N 33/18* (2013.01);
(Continued)

(58) Field of Classification Search
CPC ...... G01D 11/245; G01D 21/00; G01D 18/00; G01D 9/005; G06F 13/4086; G06F 1/1613; G06F 1/1632; G06F 1/1635; G06F 1/1684; G06F 1/26; G06F 3/0317; G06F 3/0421; G06F 9/4418; G06F 19/00; G06F 1/1601;
(Continued)

(56) References Cited

U.S. PATENT DOCUMENTS 6,943,621 B1 *   9/2005  Shuler, Jr. ............. H03F 1/0277
                                                  330/124 R
8,069,720 B2 * 12/2011  Isenmann ............. G01F 15/063
                                                  73/273
(Continued)

OTHER PUBLICATIONS

UM 10204 I2C-bus specification and user manual; Apr. 4, 2014; NXP Semiconductors; Rev. 6; pp. 1-64 (Year: 2014).*

*Primary Examiner* — Idriss N Alrobaye
*Assistant Examiner* — Richard B Franklin
(74) *Attorney, Agent, or Firm* — Polsinelli PC

(57) ABSTRACT

A modular sensor system may include a sensor bus architecture configured for interchangeable sensor modules. Stackable sensor modules, such as rods, may have input/output (I/O) connectivity. The sensor modules may interconnect with a sensor bus head, a sensor bus terminus, and/or one another. The uppermost sensor module may connect to the sensor bus head, and the lowermost sensor module may connect to the sensor bus terminus. Between the sensor bus head and the sensor bus terminus, various sensor modules may be connected. The modular arrangement of the sensors in the system of some embodiments is provided such that the sensors are interconnected through a sensor bus network. The sensor bus communication scheme may allow hot-swapping of sensors and relatively low power operation for energy-constrained sensor data collection applications.

7 Claims, 5 Drawing Sheets

(51) Int. Cl.
    *G01N 33/18*      (2006.01)
    *G01D 18/00*      (2006.01)
    *G01D 21/00*      (2006.01)
    *G06F 1/26*      (2006.01)
    *G06F 9/4401*      (2018.01)
    *G06F 13/40*      (2006.01)

(52) U.S. Cl.
    CPC ............... *G01N 33/24* (2013.01); *G06F 1/26* (2013.01); *G06F 9/4418* (2013.01); *G06F 13/4086* (2013.01); *H04Q 2209/10* (2013.01); *H04Q 2209/40* (2013.01); *H04Q 2209/82* (2013.01); *H04Q 2209/886* (2013.01); *Y02D 10/14* (2018.01); *Y02D 10/151* (2018.01)

(58) Field of Classification Search
    CPC .... G06F 1/1616; G06F 1/1626; G06F 1/1656; H04Q 2209/10; H04Q 2209/40; H04Q 2209/82; H04Q 2209/886; H04Q 9/00; H04Q 11/04; H04Q 2213/13292; H04Q 2213/13322; H04Q 2213/1336
    See application file for complete search history.

(56) References Cited

U.S. PATENT DOCUMENTS

| | | | |
|---|---|---|---|
| 9,672,186 B2* | 6/2017 | Desposito | G06F 13/4247 |
| 9,946,680 B2* | 4/2018 | Chavez | G06F 13/4282 |
| 2014/0265550 A1* | 9/2014 | Milligan | H04L 12/10 |
| | | | 307/1 |
| 2016/0127173 A1* | 5/2016 | Gagnon | H04L 12/40019 |
| | | | 709/211 |
| 2017/0366877 A1 | 12/2017 | Basheer et al. | |

* cited by examiner

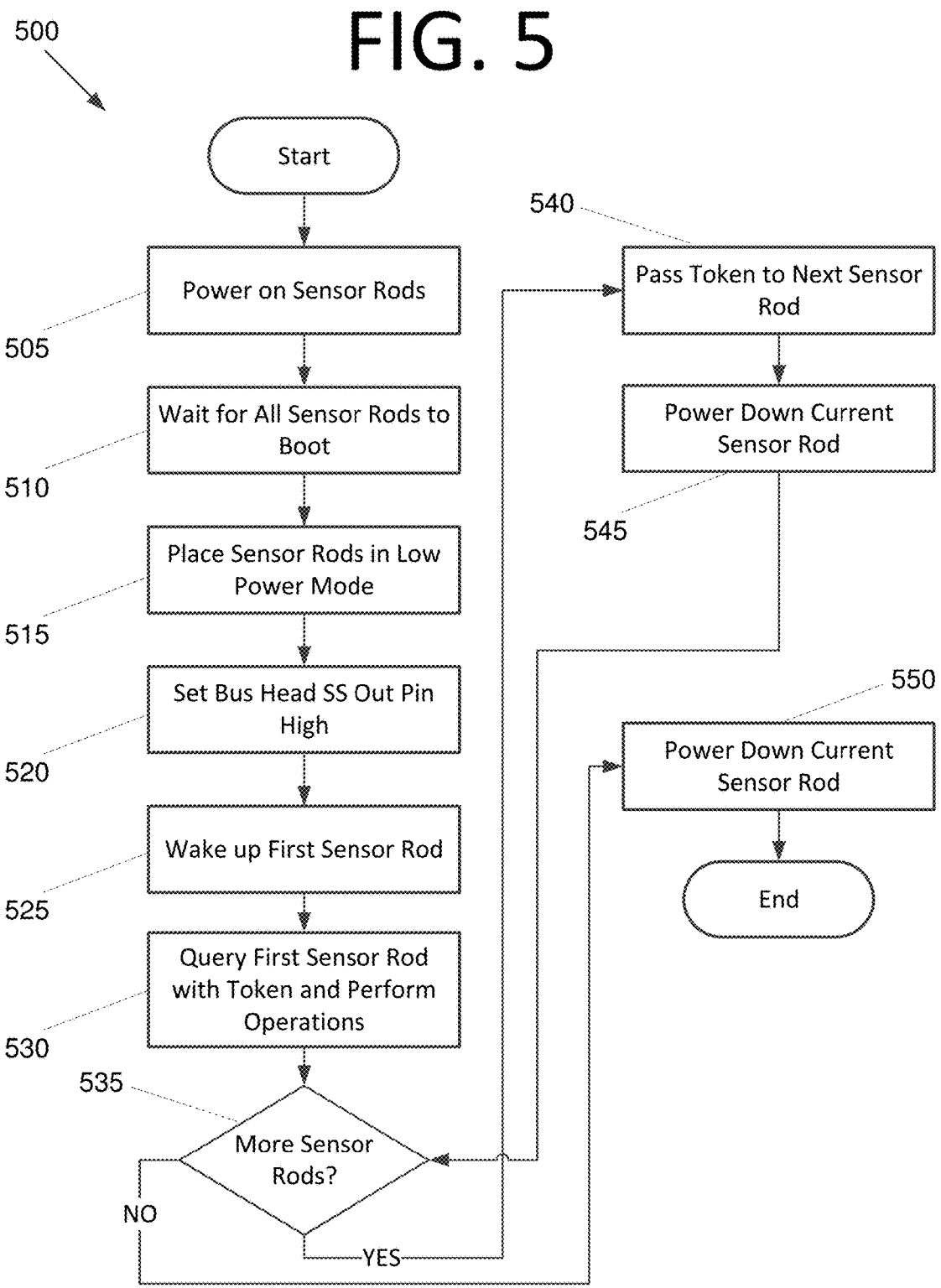

US 10,499,123 B2

SENSOR BUS ARCHITECTURE FOR MODULAR SENSOR SYSTEMS

CROSS-REFERENCE TO RELATED APPLICATIONS

This application claims the benefit of U.S. Provisional Patent Application No. 62/351,989 filed Jun. 19, 2016. The subject matter of this earlier filed application is hereby incorporated by reference in its entirety.

FIELD

The present invention generally pertains to bus architectures, and more specifically, to a sensor bus architecture for modular sensor systems.

BACKGROUND

Conventionally, sensors are designed as part of a single, non-stackable unit. Adding/removing sensors typically involves adding/removing chips from a socketed interface. Accordingly, an improved sensor architecture and bus system to accommodate the sensor architecture may be beneficial.

SUMMARY

Certain embodiments of the present invention may provide solutions to the problems and needs in the art that have not yet been fully identified, appreciated, or solved by conventional bus technologies. For example, some embodiments of the present invention pertain to a sensor bus architecture for modular sensor systems.

In an embodiment, a modular sensor system includes a sensor bus that forms a top of the modular sensor system. The sensor bus head includes processing and control circuitry and a sensor select (SS) Out pin. The modular sensor system also includes a sensor bus terminus that forms a bottom of the modular sensor system. The sensor bus terminus includes an SS In pin. The modular sensor system further includes a first sensor module interconnectable between the sensor bus head and the sensor bus terminus. The first sensor module includes an SS Out pin and an SS In pin. The sensor bus head, the sensor bus terminus, and the first sensor module are interconnectable by a sensor bus, the sensor bus comprising sensor select (SS) lines. The SS Out pin of the sensor bus head is configured to be connected to the SS In pin of the first sensor module, and the SS Out pin of the first sensor module is configured to be connected to the SS In pin of the sensor bus terminus.

In another embodiment, a sensor bus head includes processing and control circuitry and an SS Out pin. The SS Out pin of the sensor bus head is connected to an SS Out line. The SS Out pin is configured to be connected to an SS In pin of a first sensor module. The processing and control circuitry is configured to set the SS Out pin of the sensor bus head to high to wake up the first sensor module, query the first sensor module to get sensor data, pass calibration information to the first sensor module, and when the sensor bus head is done with the first sensor module, instruct the first sensor module to wake up a next sensor module in a modular stack.

In yet another embodiment, a sensor module includes an SS Out pin and an SS In pin. The sensor module is interconnectable with a sensor bus head and other sensor modules via a sensor bus. The sensor bus includes SS lines. The SS Out pin of the sensor module is configured to be connected to an SS In pin of a next sensor module in a modular stack.

BRIEF DESCRIPTION OF THE DRAWINGS

In order that the advantages of certain embodiments of the invention will be readily understood, a more particular description of the invention briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which:

FIG. 5 is a flowchart illustrating a process for communication in a stacked sensor system, according to an embodiment of the present invention.

DETAILED DESCRIPTION OF THE EMBODIMENTS

Some embodiments of the present invention pertain to a sensor bus architecture for modular sensor systems. The sensors may be included in stackable sensor modules, such as rods, with input/output (I/O) connectivity. As used herein, sensor modules are interconnectable hardware modules that include one or more sensors. In some embodiments, the sensor modules, or rods, interconnect with a sensor bus head, a sensor bus terminus, and/or one another. The uppermost sensor module may connect to the sensor bus head, and the lowermost sensor module may connect to the sensor bus terminus. Between the sensor bus head and the sensor bus terminus, various sensor modules may be connected. In certain embodiments, this may form a vertically stacked arrangement. However, in other embodiments, the sensor modules or rods may be horizontally connected or connected in any desired manner without deviating from the scope of the invention.

Each sensor rod may measure one or more specific parameters. For measuring different parameters, different sensors embedded in different sensor modules may be interconnected between the sensor bus head at the top and the sensor bus terminus at the bottom. The sensor system may then be deployed in accordance with its mission. The modular arrangement of the sensors in the system of some embodiments is provided such that the sensors are interconnected through a sensor bus network. The sensor bus communication scheme may allow hot-swapping of sensors and relatively low power operation for energy-constrained sensor data collection applications.

Figure 1:
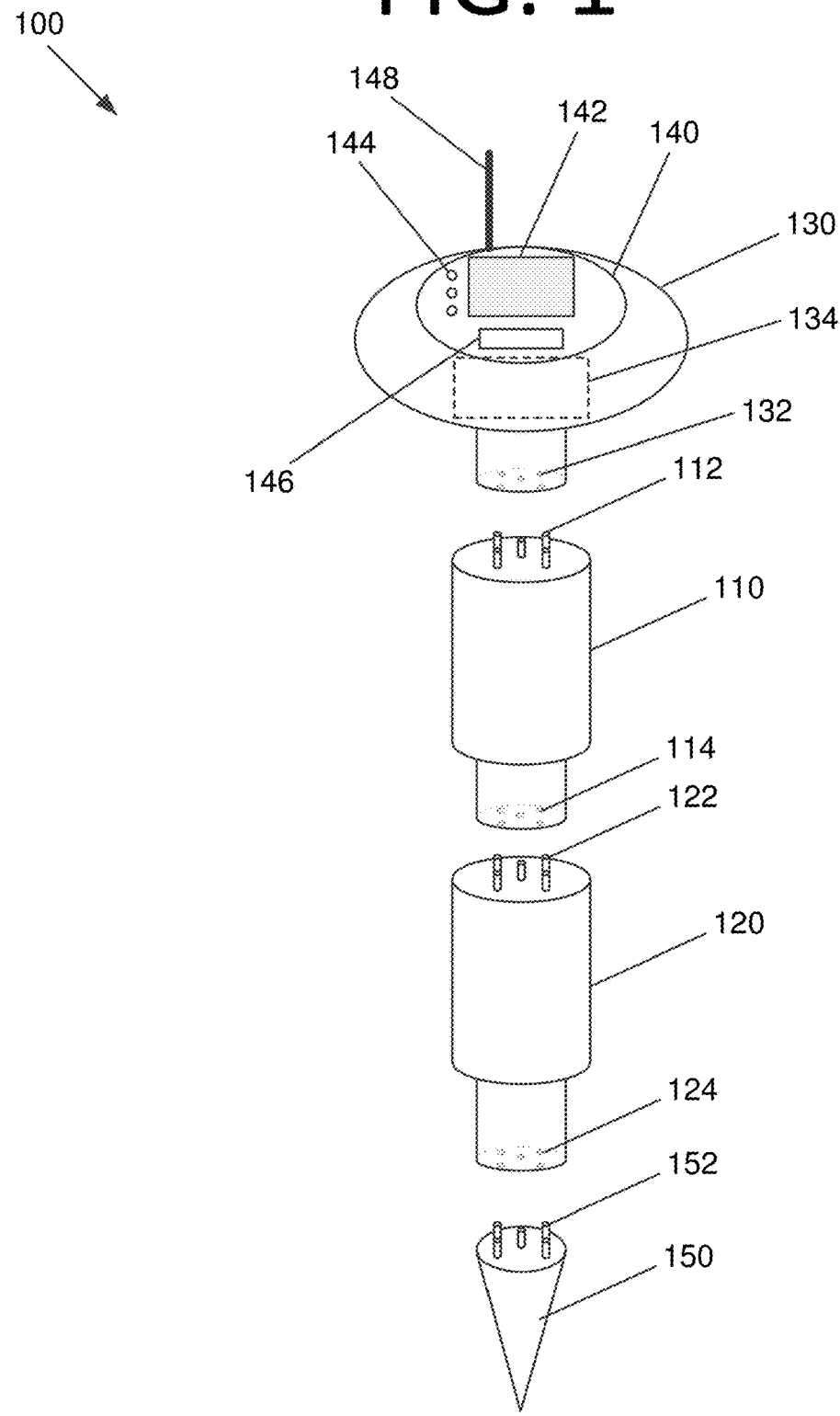
FIG. 1 is a perspective view illustrating components of a modular sensor device in a separated state, according to an embodiment of the present invention.

FIG. 1 is a perspective view illustrating components of a modular sensor device 100 in a separated state, according to an embodiment of the present invention. In this embodiment, modular sensor device 100 includes two sensor rods 110, 120 that are vertically connected to one another. Sensor rod 110 is connected to sensor bus head 130 at an upper end thereof. Sensor rod 120 is connected to a sensor bus terminus 150 at the lower end thereof. Sensor bus terminus 150 may provide loading to identify the end of the stacked sensors.

In this embodiment, sensor 110 connects to sensor bus head 130, sensor 120 connects to sensor 110, and sensor bus terminus connects to sensor 120 via male connectors 112, 122, 152, respectively (e.g., 5-pin male connectors), and female connectors 132, 114, 124, respectively (e.g., 5-pin female connectors). Alternatively, the male/female connectors may be reversed among the components (i.e., the female connectors may be on the top and the male connectors may be on the bottom), or some male connectors and some female connectors may be included on both the top and the bottom. Indeed, any suitable connectors and/or connection mechanism may be used to facilitate communication between the various components in other embodiments without deviating from the scope of the invention. As used herein, "pin" may be a port, a pin, or any other suitable connector without deviating from the scope of the invention.

Sensor bus head 130 includes processing and control circuitry 134 (e.g., a microcontroller, transceiver, etc.) that facilitates operations of sensor bus head 130. Sensor bus head 130 also includes a power and control interface 140 in this embodiment. Power and control interface 140 includes a solar panel 142 to provide power to device 100, controls 144, and a display 146 for displaying various information to the user. For instance, controls 144 and display 146 may enable a user to select a function associated with device 100. Device 100 may be designed to enable various sensor functions and analysis. Results of the analysis may be provided on display 146. In certain embodiments, sensor bus head 130 may communicate analysis results to a central server (not shown) using an antenna 148 that allows communication with other modular sensor devices, a cellular network, local area network (LAN), wide area network (WAN), or satellite communications network, for instance. An interconnected bus network runs between, and interconnects, the components of device 100, as shown in further detail in FIG. 4.

Figure 2:
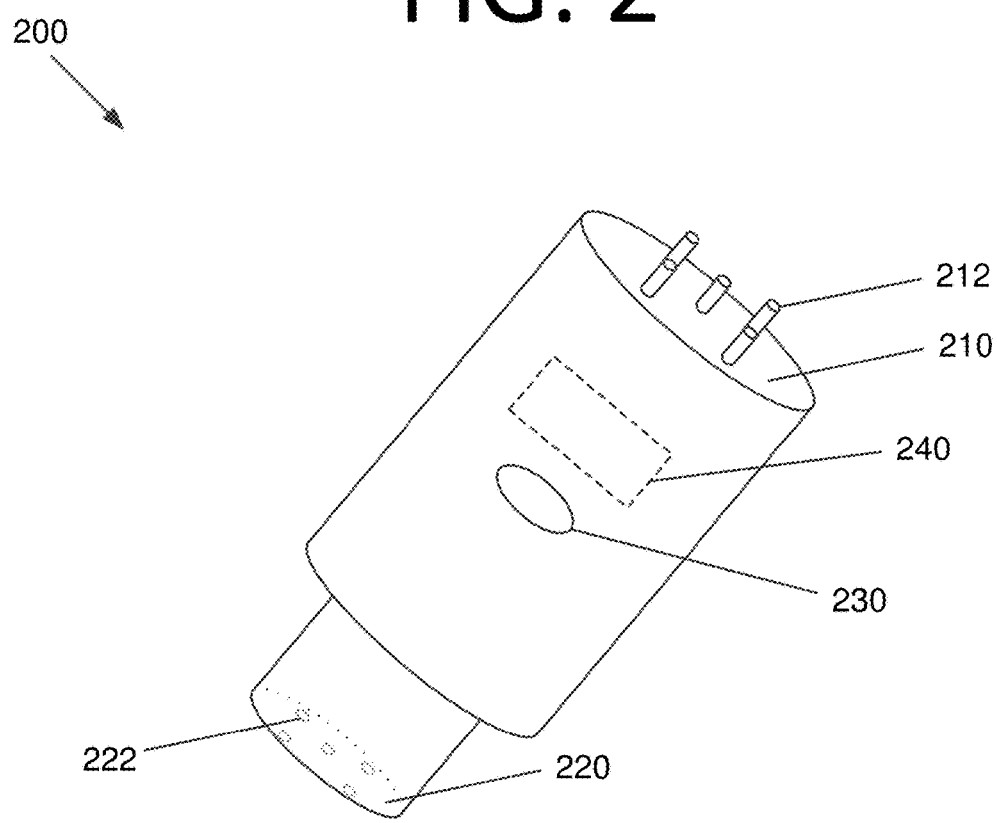
FIG. 2 is a perspective view illustrating a sensor rod, according to an embodiment of the present invention.

FIG. 2 is a perspective view illustrating a sensor rod 200, according to an embodiment of the present invention. Sensor rod 200 includes an upper section 210 including male connectors 212 and a lower section 220 including female connectors. Sensor rod 200 also includes a sensor 230 to measure various parameters. A microcontroller 240 is programmed to perform the various functions associated with sensor rod 200 and to communicate with a sensor bus head, other sensor rods, a sensor bus terminus, etc.

Figure 3:
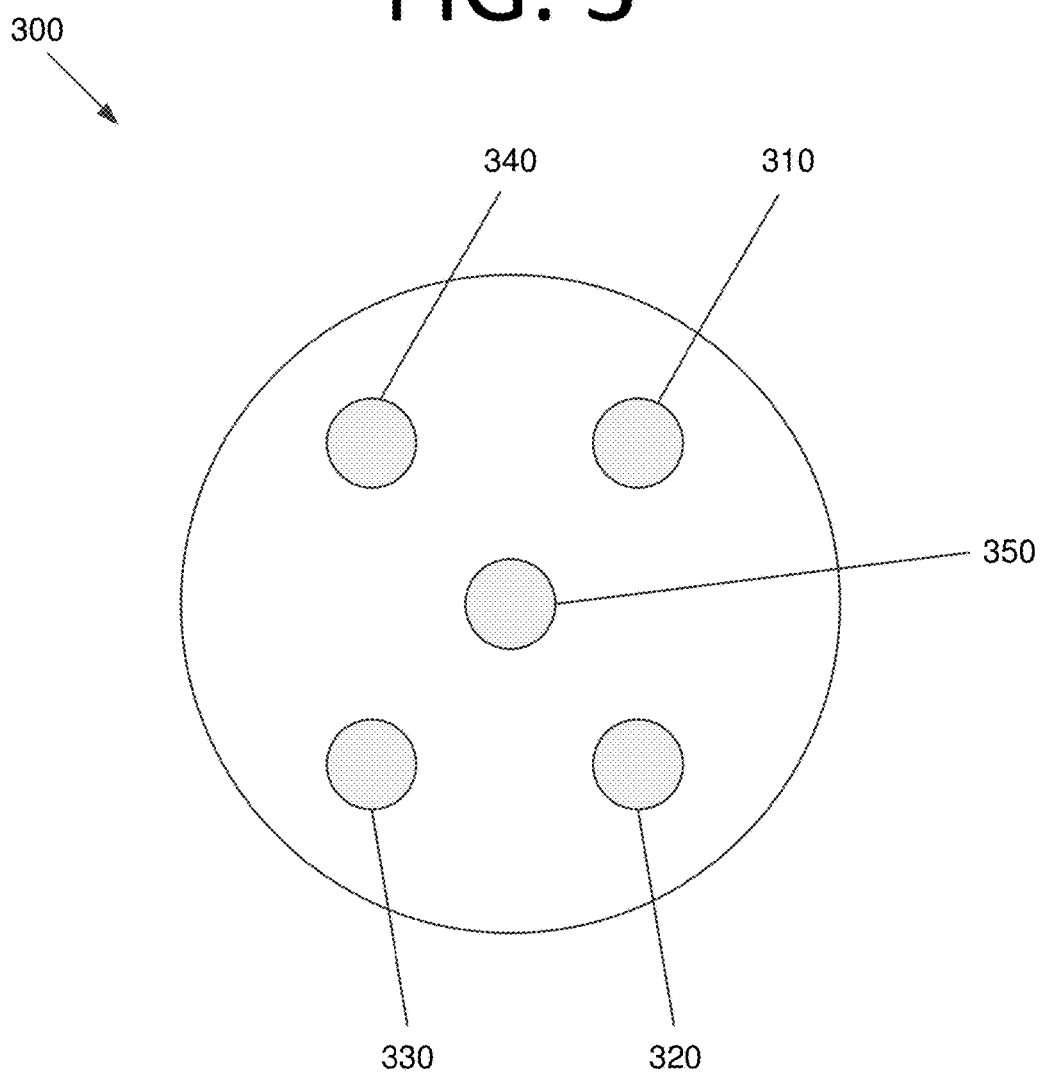
FIG. 3 is a top view illustrating connectors of a sensor rod, according to an embodiment of the present invention.

FIG. 3 is a top view illustrating connectors of a sensor rod 300, according to an embodiment of the present invention. Connector (e.g., pin) 310 is a power (Vcc) pin, where the sensor head will provide supply voltage to connector 310 when it is communicating with sensor rod 300, or other interconnected sensor rods. Connector 310 is shared by all the sensor rods present in the device in this embodiment. To save power, the sensor bus head may turn off the supply voltage when possible without interfering with sensor operations. Connector 320 is a ground (Gnd) pin, which is the reference ground for the entire system in this embodiment. Connector 320 may be shared by all sensor rods in the device. Connector 330 is a data pin that facilitates bidirectional communication between the sensor rods and the sensor bus head. Connector 340 is a clock (CLK) pin that is shared by all stacked sensor rods and is controlled by the sensor bus head. Connector 340 signals the rate at which information is clocked in and out of the sensor rods. Connector 350 is a sensor select SS pin (in/out) and is not shared by all stacked sensor rods in this embodiment. Rather, SS pins are daisy chained. See FIG. 4. Connector 350 in this embodiment is connected to the SS In pin of the stacked sensor (or sensor bus head) above it.

Figure 4:
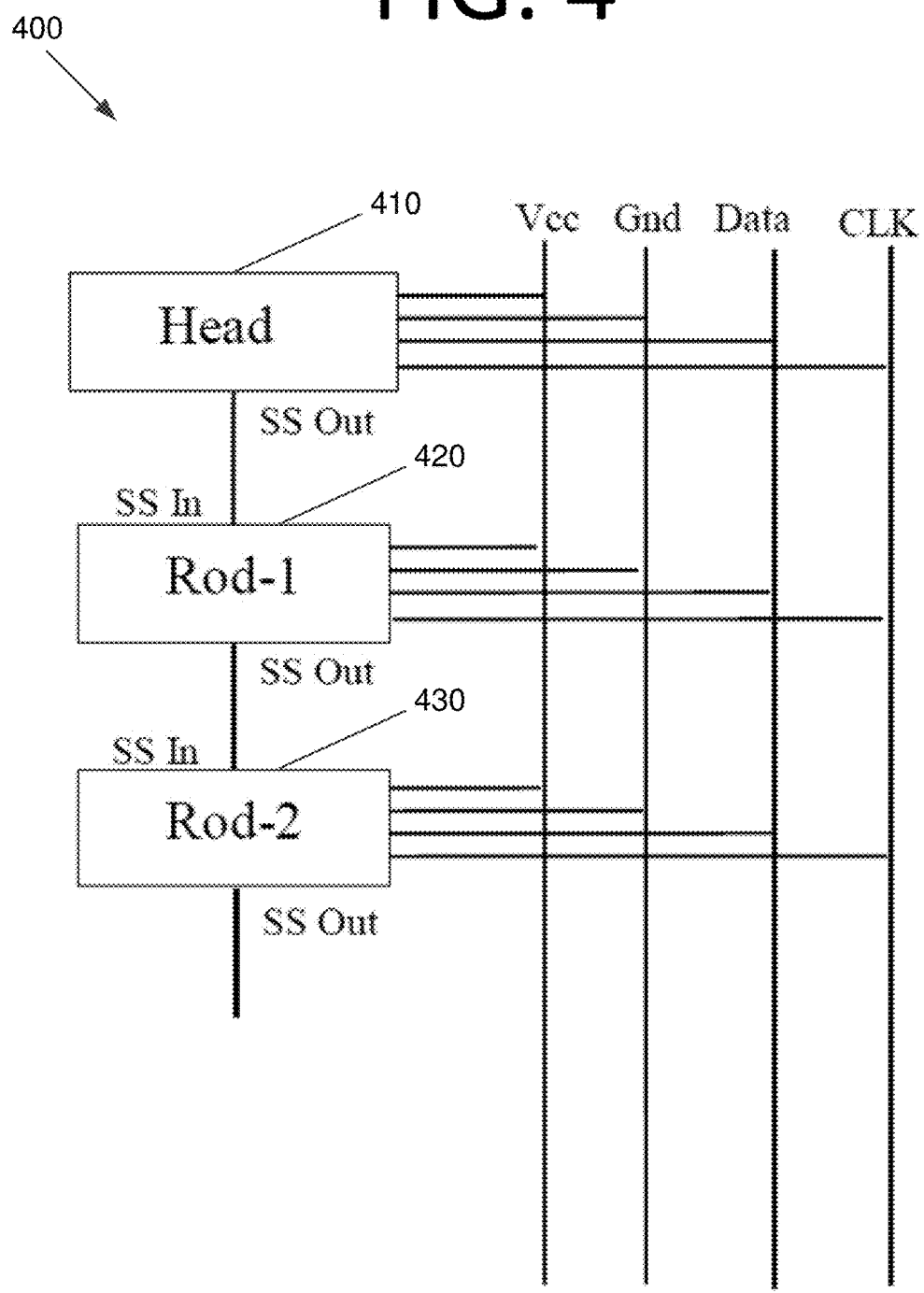
FIG. 4 is a wiring diagram illustrating bus architecture for stacked sensor rods, according to an embodiment of the present invention.

FIG. 4 is a wiring diagram 400 illustrating bus architecture for stacked sensor rods, according to an embodiment of the present invention. Sensor bus head 410 periodically communicates with sensor rods, such as sensor rods 420, 430, to query for sensor data or to instruct the system to perform certain instructions. In some embodiments, sensor rods 420, 430 may be stacked, and any desired number of sensor rods may be interconnected without deviating from the scope of the invention.

As shown in FIG. 4, all components (sensor bus head 410, sensor rod 420, and sensor rod 430) are connected to Vcc, Gnd, Data, and CLK lines. However, the SS connectors are "daisy chained" together. For instance, SS Out of sensor bus head 410 is connected to SS In of sensor rod 420, SS Out of sensor rod 420 is connected to SS In of sensor rod 430, etc. Through this configuration, individual sensor rods can be "awakened" to carry out their various functions.

FIG. 5 is a flowchart 500 illustrating a process for communication in a stacked sensor system, according to an embodiment of the present invention. The process begins with powering on the sensor rods at 505. Initially, the sensor bus head may power on the sensor rods by providing a supply voltage at a Vcc pin. This turns ON all sensor rods that are connected to the sensor bus head. The sensor bus head then waits for all of the sensor rods to power up and go through their boot up sequence at 510. At the end of the boot up sequence, the sensor rods place themselves in a low power mode where their consumed current is the minimal leakage current at 515.

More specifically, during the boot-up sequence for each sensor rod, the sensor rods setup a low-to-high transition interrupt in the SS In pin, and, in addition, set their SS Out pins to a low state. Subsequently, each sensor rod goes into a low power mode, from which it awakens only by a low-to-high transition in voltage at the SSin pin in some embodiments. After waiting for the sensor rods to finish their bootup sequence, and when the sensor bus head is ready to communicate with the first sensor rod, the sensor bus head sets its SS Out pin to high at 520. The first sensor rod, which is directly attached to the sensor bus head, then sees the transition to high in its SS In pin and wakes up from its low power state at 525. At this point, the first sensor rod is fully "awake" and able to initiate a bidirectional communication with the sensor bus head as the first sensor rod has the communication token from the sensor bus head.

As used herein, a "token" is merely an abstraction. It is not a data format or a message. Rather, the token implies that whichever sensor rod is currently able to engage in a bidirectional communication with the sensor bus head is said to have the "token." When a sensor rod is in low power mode, it doesn't have the ability to engage in communication. The way some embodiments operate is that the sensor rod that is out of low power mode and is engaged in bidirectional communication with the sensor bus head will, at the end of its communication slot, be able to wake up the next sensor rod down in the stack and then put itself into low power sleep mode. This is called "passing the token."

Since the first sensor rod is the only rod that is currently out of the low power sleep mode, it is now able to engage in bidirectional communication with the sensor bus head. The sensor bus head will now be able to query the first sensor rod to get sensor data, pass calibration information, and finally, when the sensor bus head is done with the first sensor rod, it will instruct the first sensor rod to wake up the next sensor rod in the modular stack. The first sensor rod will then place itself in low power deep sleep mode (passing the token).

The sensor bus head then queries the first sensor rod with the token at 530, which may request communication of sensor data, pass sensor calibration information, and at the end, command the first sensor rod to pass the token to the next sensor rod in the stacked sensor arrangement, etc. Passing the token is the last command from sensor bus head to the first sensor rod in this embodiment.

If there are more sensor rods at 535 (i.e., there is more than one stacked sensor rod), the first sensor rod passes the token to the next sensor rod at 540 and powers down to the low power state at 545. More specifically, on receiving the pass token command, the first sensor rod will set its SS Out pin to high, pass the token, and then go into low power mode. The process then returns to step 535 and repeats as long as there are more sensor rods. More specifically, the next stacked sensor rod in the stacked chain is awakened from its low power state by the voltage level transition in its SS In pin.

However, if there are not more sensor rods (for instance, the sensor bus head observes that a communication attempt with the next sensor rod is resulting in no response), this indicates that the end of the sensor rod stack has been reached, and there is no further sensor rod connected in the stacked arrangement. The current sensor rod (i.e., the one currently with the token) then powers down to a low power state at 550. The process of waking up sensor rods and passing tokens may be repeated periodically to perform sensor operations, receive sensor data at the sensor bus head, and communicate the sensor data.

It will be readily understood that the components of various embodiments of the present invention, as generally described and illustrated in the figures herein, may be arranged and designed in a wide variety of different configurations. Thus, the detailed description of the embodiments of the present invention, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. A modular sensor system, comprising:
a sensor bus head that forms a top of the modular sensor system, the sensor bus head comprising processing and control circuitry and a sensor select (SS) Out pin;
a sensor bus terminus that forms a bottom of the modular sensor system, the sensor bus terminus comprising an SS In pin;
a sensor module comprising a first sensor module interconnectable between the sensor bus head and the sensor bus terminus and comprising an SS Out pin and an SS In pin; and
a second sensor module,
wherein:
the sensor bus head, the sensor bus terminus, and the sensor module are interconnectable via each of a data line of a sensor bus and a daisy chain including each of the SS Out pin of the sensor bus head, the SS In pin of the sensor module, the SS Out pin of the sensor module, and the SS In pin of the sensor bus terminus,
the sensor module is configured to transition, in response to identifying a transition on the SS In pin of the sensor module, from low power mode to active mode such that, when in active mode, the sensor module is configured to bidirectionally communicate with the sensor bus head via the data line,
the first sensor module, the second sensor module, and the sensor bus terminal form at least part of a sensor stack in which the first sensor module and the second sensor module are disposed between the sensor bus head and the sensor bus terminus, and
each component of the sensor stack is connected via each of the sensor bus and the daisy chain,
wherein the processing and control circuitry of the sensor bus head is further configured to:
set the SS Out pin of the sensor bus head, wherein setting the SS Out pin of the sensor bus head results in the transition on the SS In pin of the first sensor module;
subsequent to the first sensor module transitioning to the active mode, at least one of query the first sensor module to get sensor data from the first sensor module over the data line or pass calibration information to the first sensor module over the data line;

subsequent to the first sensor module transitioning to the active mode, transmit an instruction to the first sensor module to transition the SS out pin of the first sensor module, wherein transitioning the SS out pin of the first sensor module causes the first sensor module to transition from active mode to low power mode and the second sensor module to transition from low power mode to active mode such that, when in active mode, the second sensor module is configured to bidirectionally communicate with the sensor bus head over the data line; and subsequent to the first sensor module transitioning to the active mode, at least one of query the second sensor module to get sensor data from the second sensor module over the data line or pass calibration information to the second sensor module over the data line.

2. The modular sensor system of claim 1, wherein the sensor bus further comprises a power (Vcc) line, a ground (Gnd) line, and a clock (CLK) line.

3. The modular sensor system of claim 1, wherein the sensor bus head, via the processing and control circuitry, communicates with the sensor module to at least one of query for sensor data and to awaken the sensor module.

4. A sensor module, comprising:
a microcontroller; and
each of a sensor select (SS) Out pin, an SS In pin, and a data pin electrically coupled to the microcontroller;
wherein:
the sensor module is coupleable to each of a first modular sensor system component and a second modular sensor system component, the first modular sensor system component being one of a sensor bus head and a second sensor module and the second modular sensor system component being one of a third sensor module component and a sensor bus terminus, when coupled to the first modular sensor system component and the second modular sensor system component, the sensor module is electrically coupled by the data pin to a data line of a sensor bus formed by the sensor module and the first modular sensor system component and electrically coupled by the SS In pin to a daisy chain including the first modular sensor system component, and the microcontroller is configured to, upon detecting a transition on the SS In pin, transition from low power mode to active mode, such that, when in active mode, the sensor module is configured to bidirectionally communicate over the data line, wherein the microcontroller is further configured to receive a command over the data line to activate another sensor module, and, in response to receiving the command, transition a state of the SS Out pin.

5. The sensor module of claim 4, wherein
the sensor bus further comprises a power (Vcc) line, a ground (Gnd) line, and a clock (CLK) line, and
the sensor module further comprises a power (Vcc) pin, a ground (Gnd) line, and a clock (CLK) pin.

6. The sensor module of claim 5, wherein the microcontroller is further configured to cause the sensor module to power up and go through a boot sequence upon first receiving power from the power line.

7. The sensor module of claim 6, wherein the microcontroller is configured to cause the sensor module to place itself in low power mode after the boot sequence is completed.

* * * * *